United States Patent [19]

Ishizuka et al.

[11] Patent Number: 5,166,368

[45] Date of Patent: Nov. 24, 1992

[54] PROCESS OF PRODUCING DICHLOROACETALDEHYDE TRIMER

[75] Inventors: Makoto Ishizuka, Saitama; Takashi Wakasugi, Fukushima, both of Japan

[73] Assignee: Kureha Chemical Industry Co., Ltd., Chiyoda, Japan

[21] Appl. No.: 691,473

[22] Filed: Apr. 25, 1991

[30] Foreign Application Priority Data

May 7, 1990 [JP] Japan .................................. 2-117112

[51] Int. Cl.$^5$ ............................................. C07D 323/06
[52] U.S. Cl. .................................................... 549/367
[58] Field of Search ......................................... 549/367

[56] References Cited

U.S. PATENT DOCUMENTS 3,322,792  5/1967  Centola .............................. 549/367

FOREIGN PATENT DOCUMENTS 368613  5/1990  European Pat. Off. .

OTHER PUBLICATIONS

Chemische Berichte 8, 87–88 (1875).

Primary Examiner—Nicky Chan
Attorney, Agent, or Firm—Burgess, Ryan and Wayne

[57] ABSTRACT

A process of producing a high-pure dichloroacetaldehyde trimer with high yield by cyclodehydrating dichloroacetaldehyde hydrate in the presence of concentrated sulfuric acid.

1 Claim, No Drawings

PROCESS OF PRODUCING DICHLOROACETALDEHYDE TRIMER

FIELD OF THE INVENTION

This invention relates to a process of producing a dichloroacetaldehyde trimer.

BACKGROUND OF THE INVENTION

Dichloroacetaldehyde (hereinafter, is referred to as "DCA") is useful as a synthesis raw material for medicines or agricultural chemicals and a method of producing DCA from para-acetaldehyde, acetaldehyde, or 1,2-dichloroethylene by chlorination is known. However, since DCA is a very unstable compound and very easily polymerized, it is difficult to store DCA for a long period of time as is. Accordingly, to insure stability, DCA is stored as an aqueous solution thereof or an acetal thereof but in such a case, it is difficult to obtain high pure DCA as a synthesis raw material from the aqueous solution or the acetal.

As a method capable of stably storing DCA in stable form and reproducing high pure DCA, an attempt to form a trimer of DCA is disclosed by David D. Centola et al, in U.S. Pat. No. 3,322,792. According to the method, DCA containing less than 1% by weight monochloroacetaldehyde as an impurity is heated to a temperature of from about 10° C. to about 70° C. in the presence of a metal chloride such as antimony chloride, iron chloride, aluminum chloride, tin chloride, etc., and chlorine.

However, since it is difficult to separate monochloroacetaldehyde from DCA, for preparing a mixture of chlorinated acetaldehydes, it is necessary to subject a chlorinated liquid composed of about 85% DCA, about 13% monochloroacetaldehyde, and about 2% chloral obtained by para-acetaldehyde or acetaldehyde under an ordinary condition, for obtaining DCA, to a chlorination reaction in a presence of para-toluenesulfonic acid and antimony trichloride as the catalyst as described in U.S. Pat. No. 3,150,189. However, in this method, since a metal chloride is used to catalyze the trimerization, the separation or removal of the metal chloride is troublesome and further when antimony trichloride having a relatively high trimerization yield in these metal chlorides is used, there is a problem in the recovery of non-toxic materials.

Also, as other method of forming a polymer of DCA, it has been noted that a very slight amount of a DCA polymer is formed by reacting DCA or DCA diethylacetal and sulfuric acid by Oscar Jacobsen, *Chemische Berichte*, 8, 87-88(1875) but, as a matter of course, the method can not give a yield in an amount sufficient for an industrial production process.

This invention is a novel process of producing a DCA trimer, which has been made after considering the aforesaid processes.

An object of this invention is to provide a process of producing a DCA trimer wherein the high pure DCA trimer is obtained in a high yield.

Also, another object of this invention is to provide a process of producing a DCA trimer without the need for using DCA having a low content of impurity (monochloroacetaldehyde) obtained by a specific chlorination reaction as a raw material.

Furthermore, a still further object of this invention is to provide a process of producing a DCA trimer which can be easily purified without using a metal chloride, etc., as a catalyst.

A further object of this invention is to provide an industrially useful process of producing a DCA trimer, wherein concentrated sulfuric acid used for the production of the DCA trimer can be recovered by a simple method for repeated use.

SUMMARY OF THE INVENTION

As the result of various investigations for achieving the aforesaid objects, it has been discovered that by once forming a hydrate of DCA and cyclodehydrating it with concentrated sulfuric acid, a DCA trimer can be produced without need of a specific chlorination treatment or without using a catalyst such as a metal chloride, etc.

That is, the invention is a process of producing a DCA trimer, which comprises cyclodehydrating 3 mols of a DCA hydrate in the presence of concentrated sulfuric acid.

In this invention, the aforesaid cyclodehydration may be carried out by adding a DCA hydrate to from 5 to 15 times by weight of from 95 to 99% sulfuric acid cooled to a temperature of from −20° C. to 20° C.

Also, a DCA hydrate is formed by reacting a chlorinated acetaldehyde containing at least 90% DCA with water and the aforesaid cyclodehydration may be carried out using the hydrate. Also, since the DCA trimer formed is deposited in sulfuric acid, the DCA trimer can be industrially advantageously obtained by recovering the DCA trimer thus deposited by filtration, adding hydrogen peroxide to the filtrate and heating the mixture to a temperature of at least 150° C. to remove organic materials and water, and recycling the concentrated sulfuric acid obtained for use as concentrated sulfuric acid for the cyclodehydration of the hydrate.

DETAILED DESCRIPTION OF THE INVENTION

The invention is described in detail. In addition, "%" in the following description, unless otherwise indicated, is "weight %".

The DCA hydrate as the raw material in this invention may be an industrial pure product as described above or may be DCA hydrate having a concentration of at least 90%. The raw material for use in this invention may further contain monochloroacetaldehyde hydrate, chloral hydrate, etc., in addition to DCA hydrate. Such a DCA hydrate raw material can be obtained by chlorinating para-acetaldehyde, acetaldehyde, or 1,2-dichloroethylene by a general method and treating the chlorinated liquid obtained as follows. That is, the composition of the chlorinated liquid obtained by removing unreacted materials and high-boiling components from a reaction mixture obtained by chlorinating para-acetaldehyde or acetaldehyde to a chlorination degree (a mean chlorine atom number substituted to acetaldehyde) of about 2 is composed of about 85% DCA, about 13% monochloroacetaldehyde, and about 2% chloral.

In the case of chlorinating para-acetaldehyde or acetaldehyde, usually, the chlorination rate is suddenly lowered at the chlorination degree of about 1, but from this point, by chlorinating while adding thereto water such that the temperature of the reaction mixture when the chlorination degree becomes 2 will become about 40° C., the chlorination can be carried out without an extreme reduction of the chlorination rate. After subjecting the liquid obtained by finishing the chlorination to a dehydration treatment, low-boiling components and high-boiling components are removed therefrom, whereby a chlorinated aldehyde mixture mainly composed of DCA, i.e., having a composition composed of at least 90% DCA, from 2 to 6% monochloroacetaldehyde and from 2 to 4% chloral can be obtained. In this case, as a matter of course, the contents of monochloroacetaldehyde and chloral are preferably as small as possible.

Then, by adding water to the chlorinated acetaldehyde mixture containing at least 90% DCA thus obtained in an amount of from 0.8 to 1.2 mol equivalent, and preferably from 0.9 to 1.1 mol equivalent to the content of DCA and stirring the mixture while maintaining the temperature of the mixture at a temperature of lower than 20° C., and preferably from −10° C. to 10° C., crystals mainly composed of DCA hydrate are deposited. In addition, if the amount of water being added is too small, polycondensation products are liable to be by-produced, while if the amount of water is excessive, the trimerization reaction which is carried out later is reluctant to occur.

It is preferred that the hydrate obtained is recrystallized from an organic solvent such as benzene to remove remaining water.

In this invention, the DCA hydrate thus obtained is cyclodehydrated in the presence of concentrated sulfuric acid to provide a DCA trimer. The cyclodehydration is preferably carried out by heating the DCA hydrate to a temperature of from 50° C. to 60° C. to form a molten state and gradually adding the molten hydrate to concentrated sulfuric acid cooled to a temperature −10° C. to 10° C. and by carrying out the reaction with stirring for 1 to 5 hours, a DCA trimer is deposited as crystals.

The concentration of concentrated sulfuric acid being used in this invention is at least 94%, and preferably from 95% to 99%. If sulfuric acid having a concentration of less than 94% is used, the cyclodehydration reaction does not proceed smoothly. The amount of concentrated sulfuric acid is at least 5 times by weight, and preferably from 8 to 15 times by weight the amount of the hydrate. If the amount of concentrated sulfuric acid is less than 5 times by weight, the concentrated sulfuric acid is severely colored, which makes difficult the regeneration of the concentrated sulfuric acid. On the other hand, if the amount of concentrated sulfuric acid is more than 15 times by weight, it is economically undesirable.

By the cyclodehydration, a DCA trimer is formed and the crystals thereof are deposited, and the crystals are recovered by filtration, dissolved in an organic solvent such as diethyl ether and the organic layer formed is separated. The organic layer thus obtained is washed with water and an aqueous sodium hydroxide solution and dried with anhydrous magnesium sulfate, etc., and then the crude crystals of a DCA trimer can be obtained by removing the organic solvent.

Thus, by recrystallizing the crude crystals of the DCA trimer using a mixture of hexane and alcohol, the DCA trimer having a purity of at least 99% can be easily obtained. When the crystals are heated to 160° C. under atmospheric pressure in the presence of an acid catalyst, pure DCA can be reproduced with a yield of at least 95%.

The crystals obtained by the process of this invention can be confirmed to be a DCA trimer wherein 3 molecules of DCA form a 6-membered ring by the melting point, the GC-MS analysis, the IR analysis, the elemental analysis, and the NMR analysis.

Also, after separating the DCA trimer crystals by filtration, to the filtrate (mother liquid) of the cyclodehydration reaction is added hydrogen peroxide, such as, for example, 35% hydrogen peroxide in an amount of preferably from 1 to 5% by volume and the mixture is heated to a temperature of higher than 150° C., and preferably from 190° C. to 210° C., the organic materials dissolved therein can be decomposed into non-toxic materials. Gases generated in this case are released after washing with an aqueous alkali solution and water is also simultaneously removed, thereby concentrated sulfuric acid is regenerated. The concentrated sulfuric acid thus regenerated is scarcely colored and can be recycled for use as concentrated sulfuric acid for the cyclodehydration reaction.

Then, the invention is explained more practically by the following examples.

EXAMPLE 1

(1) Preparation of Chlorinated Acetaldehyde Mixture

In a one liter three neck distillation flask equipped with a stirrer, a reflux condenser and a thermometer were placed 500 g of para-acetaldehyde and 5 ml of water and the solution was kept at 10° C. Into the solution was passed a chlorine gas at a rate of 0.15 liter/min. to initiate the reaction. Thereafter, while gradually lowering the reaction temperature to 2°±1° C., a chlorine gas was passed at a rate of from 0.15 to 0.90 liter/min. over a period of 14 hours to carry out the chlorination. In this case, when the chlorination degree reached at least 1.0, 199 g of water was gradually added to the system and the reaction temperature was raised such that the reaction temperature became 40° C. at the chlorination degree of 2. Hydrogen chloride formed was removed into an aqueous solution of sodium hydroxide.

Then, to the reaction mixture (about 1400 g) was added 300 ml of concentrated sulfuric acid and after shaking the mixture well to perform a dehydration treatment, the organic layer formed was distilled under reduced pressure (300 mm Hg), whereby DCA was concentrated.

As the result of analyzing the composition of the reaction mixture obtained by gas chromatography, it was confirmed that the product was composed of 90.5% DCA, 4.0% monochloroacetaldehyde, 3.5% chloral, and slight amounts of hydrogen chloride and high-boiling components.

(2) Synthesis of Hydrate

The synthesis of the hydrate using the chlorinated acetaldehyde mixture containing DCA as the main component was carried out using a 300 ml three neck distillation flask equipped with a stirrer and a thermometer. In the flask, to 61.2 g of the reaction mixture having the aforesaid composition was added 9 ml of water and while keeping the temperature thereof at 0° C., the mixture was stirred for one hour to deposit crystals. Then, 50 ml of benzene was added thereto followed by heating and then, the reaction mixture was cooled, whereby 60.5 g of crystals of DCA hydrate (mp. 56° C.) were obtained.

(3) Synthesis of DCA Trimer

The synthesis of the DCA trimer using the hydrate was carried out using a 500 ml 3 neck distillation flask equipped with a stirrer and a thermometer. The DCA hydrate was melted by heating to a temperature of from 50° C. to 60° C. and 25.0 g of the molten DCA hydrate was gradually added to 300 g of 96% concentrated sulfuric acid cooled to −5° C. and while keeping the mixture at a temperature of lower than 0° C., the mixture was stirred for 3 hours to provide white crystals. After the reaction was over, the crystals thus formed were recovered by filtration and dissolved in 30 ml of diethyl ether. The organic layer was repeatedly washed with water and an aqueous 10% sodium hydroxide solution and after drying with anhydrous magnesium sulfate, the solvent was distilled off under reduced pressure (20 mm Hg). By recrystallizing the crude crystals from a mixture of hexane and methanol, 12.2 g of white crystals of DCA trimer having a purity of 99.8% were obtained.

The synthesis yield of the DCA trimer was 56.4% to the hydrate. The analytical values of the white crystals are shown below.

Melting Point: 125° C.
Molecular Weight: 336 (GC-MS)
IR: 1000, 1070, 1140 cm$^{-1}$ (C-O stretching).
Elemental analysis:

|  | C | H | O | Cl |
|---|---|---|---|---|
| Calculated: | 20.90% | 1.75% | 13.92% | 63.43% |
| Found: | 21.3% | 1.7% | 14.2% | 62.4% |

$^1$H-NMR (60 MHz, CDCl$_3$): 6.5 ppm (3H, d, CH)
7.3 ppm (3H, d, CH)

(4) Reproduction of DCA

Then, 11.8 g of the DCA trimer having a purity of 99.8% was heated to 160° C. in the presence of concentrated sulfuric acid as a catalyst and distilled under atmospheric pressure. As the result of analyzing 11.3 g of the distillate by gas chromatography, it was confirmed that the distillate contained 99.9% DCA.

(5) Reproduction of Concentrated Sulfuric Acid

After the reaction was over, 1 ml of 35% hydrogen peroxide was added to 50 ml of sulfuric acid (concentration of 94.7%) colored in light brown and by carrying out the dehydration for 3 hours at 200° C. and 15 mmHg, 47.8 ml of colorless concentrated sulfuric acid (concentration of 98.2%) was regenerated.

When the synthesis of a DCA trimer was carried out using the regenerated concentrated sulfuric acid, a pure DCA trimer was obtained with the same synthesis yield as in the aforesaid example, which showed the possibility of the reuse of the generated concentrated sulfuric acid.

COMPARISON EXAMPLE

In a one liter 3 neck distillation flask equipped with a stirrer and a thermometer was placed 520 g of 96% sulfuric acid and after cooling it to −5° C., 79.1 g of DCA diethylacetal was gradually added thereto. Then, while keeping the mixture to a temperature lower than 0° C., the mixture was stirred for one hour to provide white crystals.

After the reaction was over, the crystals were recovered by filtration and dissolved in 30 ml of diethyl ether. The organic layer formed was repeatedly washed with water and an aqueous solution of 10% sodium hydroxide and after drying the organic layer using anhydrous magnesium sulfate, the solvent was distilled off under reduced pressure (20 mm Hg). By recrystallizing the crude crystals thus obtained from a mixture of hexane and methanol, 5.0 g of a DCA trimer having a purity of 99.0% was obtained. The synthesis yield for the DCA trimer was low as 11.7% to DCA diethylacetal and also since sulfuric acid after the reaction was severely colored, the purification thereof was difficult and could not be reused.

EXAMPLE 2

(1) Preparation of Chlorinated Acetaldehyde Mixture

Under the same chlorination condition for para-acetaldehyde as in Example 1, acetaldehyde was chlorinated. In the case of the chlorination, about 20% of butyl chloral was formed and hence after removing it by distillation under reduced pressure, the residue was used as the raw material chlorinated liquid for synthesizing the hydrate.

As the results of analyzing the composition of the reaction mixture thus obtained, it was confirmed that the composition was composed of 5.7% monochloroacetaldehyde, 90.2% DCA, 2.4% chloral, and slight amounts of hydrogen chloride and high-boiling components.

(2) Synthesis of Hydrate

The synthesis of the hydrate was carried out as in Example 1 using 50.6 g of the reaction mixture having the aforesaid composition and 7.2 ml water.

(3) Synthesis of DCA Trimer

The trimerization reaction was carried out as in Example 1 using 25.0 g of the hydrate and 250 g of the concentrated sulfuric acid regenerated in Example 1 and as the result thereof, 11.7 g of white crystals of DCA trimer having a purity of 99.5% were obtained.

The synthesis yield was 53.9% to the hydrate used.

Also, when the white crystals were analyzed, the IR and NMR absorption spectra had almost same patterns as in Example 1.

(4) Reproduction of DCA

By carrying out the thermal decomposition of 11.2 g of the DCA trimer having a purity of 99.5% obtained as the reproduction of DCA in Example 1, 10.8 g of DCA having a purity of 99.5% was obtained.

What is claimed is:

1. A process of producing a dichloroacetaldehyde trimer, which comprises reacting a chlorinated acetaldehyde mixture containing at least 90% by weight dichloroacetaldehyde with water to form dichloroacetaldehyde hydrate, adding the hydrate to from 5 to 15 times by weight of concentrated sulfuric acid cooled to a temperature of from −20° C. to 20° C. to carry out a cyclodehydration to form a dichloroacetaldehyde trimer, depositing the trimer, recovering the dichloroacetaldehyde trimer by filtration, adding hydrogen peroxide to the filtrate, heating the mixture to a temperature of at least 150° C. to remove organic materials and water, and recycling the concentrated sulfuric acid thus obtained for use as concentrated sulfuric acid for the cyclodehydration of the hydrate.

* * * * *

UNITED STATES PATENT AND TRADEMARK OFFICE
CERTIFICATE OF CORRECTION

PATENT NO. :  5,166,368
DATED      :  November 24, 1992
INVENTOR(S) :  Makoto Ishizuka et al.

It is certified that error appears in the above-identified patent and that said Letters Patent is hereby corrected as shown below:

On the title page:
Under Item [73] Assignee: change "Chiyoda, Japan" to --Chuo-ku, Japan--

Signed and Sealed this

Twenty-ninth Day of March, 1994

Attest:

BRUCE LEHMAN

*Attesting Officer*  *Commissioner of Patents and Trademarks*